United States Patent [19]

Baker et al.

[11] Patent Number: 4,845,101

[45] Date of Patent: Jul. 4, 1989

[54] PYRAZINE DIAZOHYDROXIDE COMPOSITIONS AND METHOD OF USE AS CYTOSTATIC AGENT

[75] Inventors: David C. Baker; Elli S. Hand, both of Tuscaloosa, Ala.; Rudiger D. Haugwitz, Bethesda; Venkatachala L. Narayanan, Gaithersburg, both of Md.; Jang B. Rampal, Fremont, Calif.

[73] Assignee: University of Alabama-Bd. of Trustees, Tuscaloosa, Ala.

[21] Appl. No.: 69,258

[22] Filed: Jul. 2, 1987

Related U.S. Application Data

[62] Division of Ser. No. 670,202, Nov. 13, 1984, Pat. No. 4,709,033.

[51] Int. Cl.$^4$ ............................................. A61K 31/495
[52] U.S. Cl. .................................................. 514/255
[58] Field of Search ......................... 544/336; 514/255

[56] References Cited

PUBLICATIONS

Baker et al., Anti-Cancer Drug Design (1987), 2, 297–309, "Synthesis, Chemical Stability and Pre-Clinical Anti-Tumor Activity of Pyrazine Diazohydroxide, Sodium Salt (NSC-361456)".
Hirschberg et al., J. Org. Chem. 1961, 26, 1907–1912.
Bunton et al., J.A.C.B. 1974, pp. 3267–3275.
Ota et al., Chem. Abst., vol 94 (1981) 120619w.
Sogo Yakuko Co. Ltd. Chem. Abst., vol. 97 (1982) 182417z.
Watanabe et al., Chem. Abst., vol. 100 (1984) 34467f.

*Primary Examiner*—Donald G. Daus
*Assistant Examiner*—Cecilia Shen
*Attorney, Agent, or Firm*—Krass & Young

[57] ABSTRACT

Chemical compounds are provided including pyrazine diazohydroxides (I), as well as methods for their production, pharmaceutical compositions comprising the compounds, and methods of treatment using the compounds in dosage form. Compounds of the invention have pharmacological properties and are useful cytostatic agents and cell growth inhibiting agents.

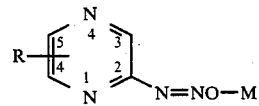

6 Claims, No Drawings

PYRAZINE DIAZOHYDROXIDE COMPOSITIONS AND METHOD OF USE AS CYTOSTATIC AGENT

This invention was made with government support under NCI Contract No. NO1-CM-27571 awarded by the Department of Health and Human Services. The government has certain rights in this invention.

This application is a division of application Ser. No. 670,202, filed Nov. 13, 1984, now U.S. Pat. No. 4,709,033.

TECHNICAL FIELD

The invention relates to chemical compounds that are pyrazine diazohydroxides, to methods for their production, to pharmaceutical compositions containing the compounds, and to methods of treatment using the compounds in dosage form. Compounds of the invention have pharmacological properties and are useful pharmacological agents, particularly cytostatic agents and cell growth inhibiting agents.

BACKGROUND OF THE INVENTION

Pyrazine diazohydroxide compounds are known in the literature as chemical intermediates, for example, as described by Hirschberg and Spoerri, *J. Org. Chem.* 1961, 26, 1907-1912, in reference to intermediates such as 2-pyrazine diazohydroxide, sodium salt. The compounds can exist in the syn and anti forms, and the invention contemplates both of these forms and mixtures thereof.

SUMMARY OF THE INVENTION

The invention in one aspect relates to specifically novel pyrazine diazohydroxide compounds having the formula I:

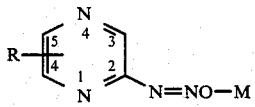

where M is a molar equivalent of an alkali metal (Group 1a metal), preferably sodium or potassium, or a half-equivalent of an alkaline earth metal (Group 2a metal), preferable calcium or magnesium, and the R-substitution is H, 3-methyl, 5-bromo, 3,6-dimethyl, 5,6-diphenyl or 3,5-bis(phenylthio), with the proviso that M in this context is a metal other than sodium where R is H, 3-methyl or 3,6-dimethyl. Preferred compounds of the invention are 2-pyrazine diazohydroxide, potassium salt; 3-methyl-2-pyrazine diazohydroxide, potassium salt; 5-bromo-2-pyrazine diazohydroxide, sodium salt; 3,6-dimethyl-2-pyrazine diazohydroxide, potassium salt; 5,6-diphenyl-2-pyrazine diazohydroxide, sodium salt; and 3,5-bis(phenylthio)-2-pyrazine diazohydroxide, sodium salt.

The invention in one method aspect includes a process for preparing pyrazine diazohydroxide compounds having the above formula I which comprises reacting an aminopyrazine compound having the formula II:

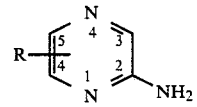

where R has the above meaning, with a base selected from alkali metal hydroxides, amides and organometallic compounds contained in an inert solvent; treating the reaction mixture with alkyl nitrite until diazotization is complete; and isolating the diazotization product from the reaction mixture in salt form.

The method is subject to considerable variation both in reactants and reaction conditions, preferably using substantially equimolar amounts of the reactants. Any of various bases can be used including alkali metal and alkaline earth metal alkoxides, amides and organometallic compounds. Sodium amide is a preferred base and potassium amide can also be used. Lower ($C_1$ to $C_4$) alkyl lithium or sodium compounds are preferred organometallic bases. To convert the metal ion to a different ion for purposes of isolating the product, ion-exchange chromatography is suitably employed preferably using a given alkali metal or alkaline earth metal salt column respectively of, for example, a sulfonic acid cation-exchanged resin. The alkyl nitrite reagent suitably is selected from lower alkyl ($C_1$ to $C_6$) nitrates which include, for example, methyl, ethyl, propyl, n-butyl, and n-pentyl nitrites. Isoamyl nitrite is a preferred nitrite. The solvent suitably comprises tetrahydrofuran (THF), ethyl ether, dioxane, dimethoxyethane or other alkyl mono-, di- or polyether solvent, THF being a preferred solvent. The reaction temperature is not critical. Temperatures in the range from 10 to 100 degrees C. can suitably be used, temperatures in the range of about 18 to about 28 degrees C. being preferred. Reaction times of from about 10 to 20 hours are generally required.

The invention in one composition aspect relates to a pharmaceutical composition for inhibiting the growth of cells in animals exemplified by rodents such as the mouse, comprising a cell growth inhibiting amount of an alkali metal or alkaline earth metal salt of the 2-pyrazine diazohydroxide compound having the above formula I as defined and additionally where M may be sodium, preferably 2-pyrazine diazohydroxide, sodium salt, potassium salt, calcium salt or magnesium salt, and a pharmaceutically acceptable carrier.

The invention in another method aspect relates to a method for inhibiting the growth of cells which comprises administering a cell growth inhibiting amount of an alkali metal or alkaline earth metal salt of the 2-pyrazine diazohydroxide compound having the above formula I as defined and additionally where M may be sodium, preferably 2-pyrazine diazohydroxide, sodium salt, potassium salt, calcium salt, or magnesium salt, in dosage form to an animal exemplified by a rodent such as the mouse, in need thereof.

PHYSICAL AND PHARMACOLOGICAL PROPERTIES OF THE COMPOUND

According to the invention, it is found that the compounds of the aforesaid pharmaceutical compositions of the invention possess useful cytostatic properties and cytotoxic properties (i.e., cell growth inhibiting properties) and are inventively useful as pharmacological agents in dosage form for the inhibition of unwanted cell growth in animals. The activity of the compounds is established by art-recognized test protocols such as the in vivo lymphocytic leukemia P388 test. The animals used are either male or female $CD_2F_1$ mice, six or seven animals per test group. The cell transplant is by intraperitoneal injection of dilute ascitic fluid containing cells of lymphocytic leukemia P388. The test compound is administered intraperitoneally once daily for five consecutive days at various doses following cell innoculation. The animals are weighed and survivors are recorded on a regular basis for 30 days. A ratio of survival time for treated (T)/ control (C) animals is calculated. A criterion for efficiency is a ratio T/C times 100 greater than or equal to 125. In this test, the compounds described herein were effective in meeting this criterion of efficacy, as tabulated below.

Table

| Pyrazine Diazohydroxides Cell Growth Inhibiting Efficacy | | |
|---|---|---|
| R | T/C | (mg/kg) |
| H—,Na+ salt | 207 | (25) |
| 3,6-di-Me, Na+ salt | 133 | (25) |
| 5,6-di-Ph, Na+ salt | 145 | (50) |
| 3-Me, Na+ salt | 142 | (50) |
| 5-Br, Na+ salt | 167 | (100) |
| 3,5-bis-PhS, Na+ salt | 140 | (50) |
| H—, K+ salt | 224 | (50) |

It is a feature of the invention that the compounds are obtainable in stable solid form. Preferred compositions are aqueous compositions of 2-pyrazine diazohydroxide in the sodium salt form or the potassium salt form, which compositions it is found are advantageously stable for relatively long periods, having for example a half-life ($t_{0.5}$) of about 100 minutes at pH 7.4 in water with an expected half-life of about 2 to 3 months at pH 10.

PREPARATION OF PHARMACEUTICAL COMPOSITIONS

When used as a pharmacological agent or pharmaceutical composition, the compounds of the composition aspect of the invention can be prepared and administered in any of a wide variety of topical, oral, and parenteral dosage forms.

For preparing pharmaceutical compositions, one uses an inert, pharmaceutically acceptable carrier which carrier can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the compound is mixed with carrier having the necessary binding properties in suitable proportion and compacted in the shape and size desired. The powders and tablets preferably contain from 5 or 20 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, e.g., natural or synthetic gums, resins, methyl cellulose, sodium carboxymethyl cellulose, and other suspending agents.

Topical preparations include dusting powders, creams, lotions, gels, and sprays. These various topical preparations may be formulated by well-known procedures. See for example Remington's Pharmaceutical Sciences, Chapter 43, 14th Ed., Mack Publishing Co., Easton, Pa. 18042, U.S.A.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 50 mg to 500 mg according to the particular application and the potency of the active ingredient.

In therapeutic use as pharmacological agents the compounds utilized in the pharmaceutical method of this invention is administered at the initial dosage of about 0.1 mg to about 50 mg per kilogram. A dose range of about 0.5 mg to about 10 mg per kilogram is preferred. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compound may also be administered parenterally or intraperitoneally. Solutions of the compound can be prepared in water mixed if desired with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugar or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorproated into the compositions.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the compound is generally present in from about 0.1 to about 500 mg/ml of carrier. In the case of compositions containing supplementary active ingredients, the dosages are determined by reference to the usual dose and the manner of administration of the said ingredients. The daily parenteral doses ranges from 0.1 mg/kg to 10 mg/kg. The preferred daily dose range is 0.3 mg/kg to 10 mg/kg. The preferred daily dose range is 0.3 mg/kg to 10 mg/kg.

The invention and the best mode of practicing the same are illustrated by the following examples.

EXAMPLE 1

2-Pyrazine Diazohydroxide, Potassium Salt:

(a) 4.75 g (0.05 mol) of 2-aminopyrazine is added to a suspension of 2.95 g (0.05 mol) of sodium amide in 40 mL of dry tetrahydrofuran (THF) maintained under a dry nitrogen atmosphere. The resulting colored mixture is stirred for an additional 30 min, followed by the dropwise addition of 6.7 mL (0.05 mol) of isoamyl nitrite dissolved in 10 mL of dry THF over a period of 10–15 min. The mixture is allowed to continue to stir vigorously for an additional 12 h, at a temperature of 23±5 °C. The product in solid form, 2-pyrazine diazohydroxide, sodium salt, is collected by filtration, washed with dry ethyl ether (3×20 mL), and recrystallized from methanol/ether.

Yield: 6.5 g (89%).

Anal. Calcd for $C_4H_3N_4ONa$: C, 32.88; H, 2.06; N, 38.35; Na, 15.73. Found: C, 32.62; H, 2.14; N, 38.08; Na, 14.98.

(b) The sodium salt product of paragraph 1(a) in aqueous solution (1.5 g in 10 mL of water) is passed over an ion-exchange column containing Amberlite IR-120 resin [K+] (potassium salt of sulphonic acid), eluted with water and the title product recovered by concentrating the eluate to dryness under vacuum, Yield 84.3%.

Anal. Calcd for $C_4H_3N_4OK$: C, 29.62; H, 1.86; N, 34.54; K, 24.10. Found: C, 29.51; H, 1.92; N, 34.43; K, 24.15.

The product can also be prepared using the procedure of paragraph 1(a) but replacing sodium amide with the potassium salt of an appropriate base (potassium amide preferred; potassium methoxide, tertiary-butoxide or hydride, or alkyl ($C_1$ to $C_4$) potassium). The foregoing procedures can also be used, e.g. by appropriate selection of the desired metal ion exchange material, to prepare any desired alkaline earth metal salt of any alkali metal salt other than sodium or potassium.

EXAMPLES 2(a) to 2(h)

By the same procedures, the following pyrazine diazohydroxides as the alkali metal salt or alkaline earth salt are prepared starting from the appropriate 2-aminopyrazine, as follows:

|      | 2-Aminopyrazine    | Pyrazine Diazohydroxide Salt                                                     |
| ---- | ------------------ | -------------------------------------------------------------------------------- |
| (2a) | 3,6-Dimethyl       | 3,6-Dimethylpyrazine-2-diazohydroxide, potassium salt or calcium salt            |
| (2b) | 5,6-Diphenyl       | 5,6-Diphenylpyrazine-2-diazohydroxide, sodium-salt or magnesium salt             |
| (2c) | 5,6-Diphenyl       | 5,6-Diphenylpyrazine-2-diazohydroxide, potassum salt or calcium salt             |
| (2d) | 3-Methyl           | 3-Methylpyrazine-2-diazohydroxide, potassium salt or magnesium salt              |
| (2e) | 5-Bromo            | 5-Bromopyrazine-2-diazohydroxide, sodium salt or calcium salt                    |
| (2f) | 5-Bromo            | 5-Bromopyrazine-2-diazohydroxide, potassium salt or magnesium salt               |
| (2g) | 3,5-Bis(phenylthio) | 3,5-Bis(phenylthio) pyrazine-2-diazohydroxide, sodium salt or                   |

PHARMACEUTICAL COMPOSITIONS

The following representative Examples 3 through 7, are given as illustrative pharmaceutical compositions utilizing different carriers. In these examples, Example 3 illustrates the use of the compounds of the invention in injectables suitable for intravenous injection. Example 4 describes an oral syrup preparation, Example 5 an oral capsule preparation and Example 6, oral tablets. Example 7 is directed to use of the compounds of the invention in suitable suppositories. For Examples 3 through 7, the ingredients are listed followed by the methods of preparing the compositions.

EXAMPLE 3

Injectables

Pyrazine-2-diazohydroxide, sodium salt
  125 mg–500 mg
Water for Injection USP q.s.

The salt compound is dissolved in the water and passed through a 0.22 micron filter. The filtered solution is added to ampoules or vials, sealed and sterilized.

EXAMPLE 4

250 mg Active ingredient/5 ml syrup

Pyrazine-2-diazohydroxide, potassium salt: 25 g
Purified Water USP: 200 ml
Cherry Syrup q.s. or: 1000 ml The salt compound is dissolved in the water and to this solution the syrup is added with mild stirring.

EXAMPLE 5

Capsules 50 mg, 125 mg or 250 mg
  5-Bromopyrazine-2-diazohydroxide, potassium salt: 500 g
Lactose USP. Anhydrous q.s. or: 200 g
Sterotex Powder HM: 5 g Combine the salt and the lactose in a twin-shell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg, 352.5 mg or 705 mg of the blend, respectively, for the 50 mg, 125 mg and 250 mg containing capsules.

EXAMPLE 6

Tablets 50 mg, 100 mg or 250 mg
  3,6-Dimethylpyrazine-2-diazohydroxide, sodium salt: 250 g
Corn Starch NF: 200.0 g
Cellulose, Microcrystalline: 46.0 g
Sterotex Powder HM: 4.0 g
Purified Water q.s. or: 300.0 ml Combine the corn starch, the cellulose and the salt compound together in a planetary mixer and mix for two minutes. Add the water to this combination and mix for one minute. The resulting mix is spread on trays and dried until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 150 mg, 357 mg and 750 mg respectively, of the total mix are formed with appropriate sized punches for the 50 mg, 125 mg or 500 mg containing tablets.

EXAMPLE 7

Suppositories 125 mg, 250 mg or 500 mg per 3 g

| 5,6-Diphenylpyrazine-2-diazohydroxide, sodium salt | 125 mg | 250 mg | 500 mg |
|---|---|---|---|
| 1540 Polyethylene Glycol | 1925 mg | 1750 mg | 1400 mg |
| 8000 Polyethylene Glycol | 825 mg | 750 mg | 600 mg |

Melt the Polyethylene Glycol 1540 and the Polyethylene Glycol 8000 together at 60° C. and dissolve the salt compound into the melt. Mold this total at 25° C. into appropriate suppositories.

Having described the invention, the embodiments of the invention in which an exclusive property or privilege is claimed are defined as follows:

1. A composition for inhibiting the growth of cells comprising in pharmaceutically acceptable dosage form an effective leukemic cell growth inhibiting amount of a 2-pyrazine diazohydroxide compound and a pharamaceutically acceptable carrier, the pyrazine diazohydroxide compound having the formula I:

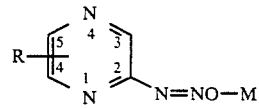

where M is an equivalent of an alkali metal or a half-equivalent of an alkaline earth metal and the R-substitution is H, 3-methyl, 5-bromo, 3,6-dimethyl, 5,6-diphenyl or 3,5-bis(phenylthio).

2. A pharmaceutical composition according to claim 1 comprising 2-pyrazine diazohydroxide, potassium salt.

3. A pharmaceutical composition according to claim 1 comprising 2-pyrazine diazohydroxide, sodium salt.

4. A method for inhibiting the growth of leukemia cells in a mammal which comprises administering a leukemic cell growth inhibiting amount of a 2-pyrazine diazohydroxide compound having the formula I according to claim 1 in pharmaceutically acceptable dosage form to the mammal.

5. A method according to claim 4 where the pyrazine diazohydroxide comprises 2-pyrazine diazohydroxide, potassium salt.

6. A method according to claim 4 wherein 2-pyrazine diazohydroxide, sodium salt is administered.

* * * * *

UNITED STATES PATENT AND TRADEMARK OFFICE
CERTIFICATE OF CORRECTION

PATENT NO. : 4,845,101

DATED : July 4, 1989

INVENTOR(S) : Baker et al

It is certified that error appears in the above-identified patent and that said Letters Patent is hereby corrected as shown below:

On the title page:

On the face of the patent, in the Abstract, the equation should read as follows: -- 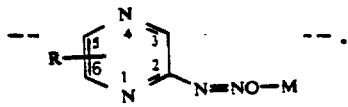 --.

Column 1, line 41-45, the equation should read as follows:

-- 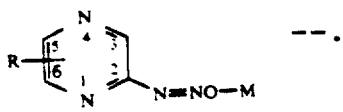 --.

Column 2, line 1-7, the equation should read as follows:

-- 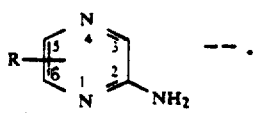 --.

Column 8, lines 33-39, the equation should read as follows:

-- 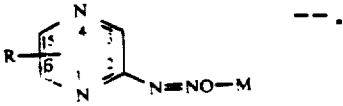 --.

UNITED STATES PATENT AND TRADEMARK OFFICE
CERTIFICATE OF CORRECTION

PATENT NO. : 4,845,101
DATED : July 4, 1989
INVENTOR(S) : Baker, et al.

It is certified that error appears in the above-identified patent and that said Letters Patent is hereby corrected as shown below:

Column 5, line 42, "incorproated" should be --incorporated--

Column 8, line 5, "357" should be --375--.

Signed and Sealed this

Eighth Day of May, 1990

Attest:

HARRY F. MANBECK, JR.

*Attesting Officer*          *Commissioner of Patents and Trademarks*

UNITED STATES PATENT AND TRADEMARK OFFICE
CERTIFICATE OF CORRECTION

PATENT NO. : 4,845,101

DATED : July 4, 1989

INVENTOR(S) : Baker et al

It is certified that error appears in the above-identified patent and that said Letters Patent is hereby corrected as shown below:

Column 8, line 31, "pharamaceutically" should be --pharmaceutically--.

Signed and Sealed this

Third Day of July, 1990

Attest:

Attesting Officer

HARRY F. MANBECK, JR.

Commissioner of Patents and Trademarks